(12) United States Patent
Minagawa et al.

(10) Patent No.: US 10,786,812 B2
(45) Date of Patent: Sep. 29, 2020

(54) MEDICAL ANALYSIS DEVICE AND CELL ANALYSIS METHOD

(71) Applicants: SUMITOMO RUBBER INDUSTRIES, LTD., Kobe-shi, Hyogo (JP); YAMAGATA UNIVERSITY, Yamagata-shi, Yamagata (JP)

(72) Inventors: Yasuhisa Minagawa, Kobe (JP); Masaru Tanaka, Yamagata (JP); Takashi Hoshiba, Yamagata (JP); Tomokazu Shibuya, Yamagata (JP)

(73) Assignees: SUMITOMO RUBBER INDUSTRIES, LTD., Kobe-Shi, Hyogo (JP); YAMAGATA UNIVERSITY, Yamagata-Shi, Yamagata (JP)

( * ) Notice: Subject to any disclaimer, the term of this patent is extended or adjusted under 35 U.S.C. 154(b) by 50 days.

(21) Appl. No.: 15/495,412

(22) Filed: Apr. 24, 2017

(65) Prior Publication Data
US 2017/0320056 A1  Nov. 9, 2017

(30) Foreign Application Priority Data

May 9, 2016 (JP) .................. 2016-093936
Aug. 19, 2016 (JP) .................. 2016-161309

(51) Int. Cl.
| | |
|---|---|
| B01L 3/00 | (2006.01) |
| G01N 33/49 | (2006.01) |
| G01N 15/10 | (2006.01) |
| G01N 15/14 | (2006.01) |
| C12Q 1/24 | (2006.01) |

(52) U.S. Cl.
CPC ......... B01L 3/50273 (2013.01); B01L 3/5021 (2013.01); C12Q 1/24 (2013.01); G01N 33/491 (2013.01); B01L 2200/0647 (2013.01); B01L 2300/0681 (2013.01); B01L 2300/165 (2013.01); B01L 2400/0409 (2013.01); G01N 15/1468 (2013.01); G01N 2015/1006 (2013.01)

(58) Field of Classification Search
None
See application file for complete search history.

(56) References Cited

U.S. PATENT DOCUMENTS

| | | | |
|---|---|---|---|
| 2002/0123134 A1* | 9/2002 | Huang | B01J 19/0046 435/287.2 |
| 2003/0203991 A1 | 10/2003 | Schottman et al. | |
| 2007/0160503 A1* | 7/2007 | Sethu | A61M 1/3633 422/400 |
| 2011/0076754 A1 | 3/2011 | Frey et al. | |
| 2013/0190212 A1* | 7/2013 | Handique | B01L 3/502715 506/37 |
| 2015/0125879 A1* | 5/2015 | Li | G01N 33/54366 435/7.23 |
| 2015/0266023 A1 | 9/2015 | Fuchiwaki et al. | |

FOREIGN PATENT DOCUMENTS

| | | |
|---|---|---|
| EP | 2720039 A1 | 4/2014 |
| JP | 2001-137613 A | 5/2001 |
| JP | 2005-523981 A | 8/2005 |
| JP | 2008-76306 A | 4/2008 |
| JP | 2009-514674 A | 4/2009 |
| JP | 2012-178539 A | 9/2012 |
| WO | WO 2006/077695 A1 | 7/2006 |
| WO | WO 2007/056338 A2 | 5/2007 |
| WO | WO 2014/051033 A1 | 4/2014 |
| WO | WO-2015002975 A1 * | 1/2015 ......... G01N 21/6428 |

OTHER PUBLICATIONS

Wang, H. et al. 2014. Carboxybetaine methacrylate-modified nylon surface for circulating tumor cell capture. ACS Applied Materials & Interfaces 6: 4450-4559. specif. pp. 4550, 4551.*
Surman, F. et al. Jan. 21, 2015. Polymer brushes interfacing blood as a route toward high performance blood contacting devices. Macromolecular Bioscience 15: 636-646. specif. pp. 636, 645.*
Casavant et al., "A Negative Selection Methodology Using a Microfluidic Platform for the Isolation and Enumeration of Circulating Tumor Cells", Methods. vol. 64, pp. 137-143, 2013.
Minelli et al., "A Micro-Fluidic Study of Whole Blood Behaviour on PMMA Topographical Nanostructures", Journal of Nanobiotechnology, vol. 6, No. 3, 11 pages, 2008.

* cited by examiner

*Primary Examiner* — Renee Claytor
*Assistant Examiner* — Sharon M. Papciak
(74) *Attorney, Agent, or Firm* — Birch, Stewart, Kolasch & Birch, LLP

(57) ABSTRACT

Provided are a medical analysis device and a cell analysis method which can capture many cancer cells, including cancer cells not expressing EpCAM. The medical analysis device includes a flow channel zone, and also includes a chamber zone. The inner surface of the flow channel zone is at least partially provided with a layer of a hydrophilic polymer having a thickness of 2 to 200 nm.

7 Claims, 1 Drawing Sheet

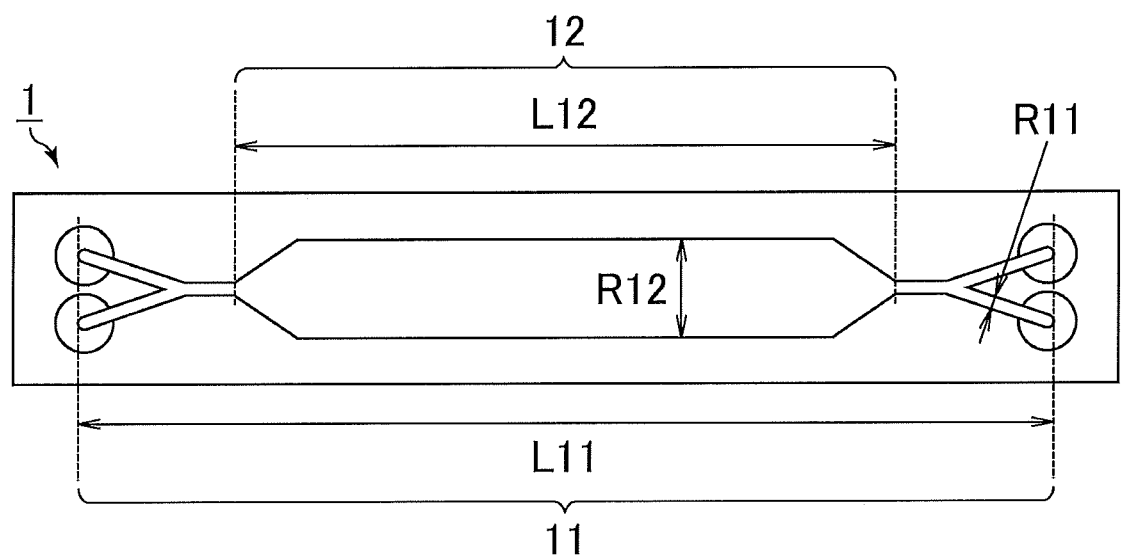

MEDICAL ANALYSIS DEVICE AND CELL ANALYSIS METHOD

TECHNICAL FIELD

The present invention relates to a medical analysis device and a cell analysis method which can capture specific cells from blood or biological fluid (e.g. blood cells, cancer cells present in blood or biological fluid).

BACKGROUND ART

When cancer cells are formed, they are known to appear in due course in blood and biological fluid. The cancer cells appearing in blood are called "circulating tumor cells (CTCs)". Thus, it is expected that such circulating tumor cells can be examined, e.g., to confirm a cancer-treating effect, predict prognosis life expectancy, predict the effect of anticancer drugs before administration, or examine treatment methods through genetic analysis of cancer cells.

However, a problem exists in that since the number of circulating tumor cells is very small (several to hundreds of cells/1 mL of blood), such cancer cells are difficult to capture.

For example, the CellSearch System is known as a technique for capturing circulating tumor cells. This technique, which utilizes an antigen-antibody reaction (capture by EpCAM antibody), can only capture cancer cells expressing EpCAM, and the types of capturable cancer cells are limited.

CITATION LIST

Patent Literature

Patent Literature 1: JP 2005-523981 T

SUMMARY OF INVENTION

Technical Problem

The present invention aims to solve the above problem and provide a medical analysis device and a cell analysis method which can capture many cancer cells, including cancer cells not expressing EpCAM.

Solution to Problem

The present invention relates to a medical analysis device, including a flow channel zone that includes a chamber zone, an inner surface of the flow channel zone being at least partially provided with a layer of a hydrophilic polymer having a thickness of 2 to 200 nm.

The hydrophilic polymer is preferably at least one selected from the group consisting of polyacrylic acid, polyacrylic acid esters, polymethacrylic acid, polymethacrylic acid esters, polyacryloylmorpholine, polymethacryloylmorpholine, polyacrylamide, and polymethacrylamide.

The hydrophilic polymer is preferably a copolymer of at least one hydrophilic monomer and a second monomer, the at least one hydrophilic monomer being selected from the group consisting of acrylic acid, acrylic acid esters, methacrylic acid, methacrylic acid esters, acryloylmorpholine, methacryloylmorpholine, acrylamide, and methacrylamide.

The flow channel zone is preferably formed from at least one material selected from the group consisting of acrylic resins, cycloolefin resin, carbonate resin, and styrene resin.

Preferably, the inner surface of the flow channel zone at least partially has a contact angle of 25° to 65° with water.

The inner surface of the flow channel zone is preferably provided with a layer of a superhydrophilic polymer in addition to or separately from the hydrophilic polymer layer.

The superhydrophilic polymer layer is preferably formed of a betaine polymer.

The medical analysis device preferably further includes a filter structure, pillar structure, or dish structure (dish-like concave structure) for screening cells.

The present invention relates to a cell analysis method, including examining cells captured from blood or biological fluid using the above medical analysis device. Preferably, blood from which platelets and red blood cells have been removed is introduced into the flow channel zone of the medical analysis device. The removal of platelets and red blood cells is preferably carried out by centrifugation.

Advantageous Effects of Invention

The medical analysis device of the present invention includes a flow channel zone that includes a chamber zone, and the inner surface of the flow channel zone is at least partially provided with a layer of a hydrophilic polymer having a thickness of 2 to 200 nm. Such a device can capture many cancer cells, including cancer cells not expressing EpCAM. With this device, for example, specific cells such as cancer cells can be sufficiently captured from blood or biological fluid, and at the same time, adhesion or attachment of other proteins and cells can also be reduced. Therefore, specific cells such as cancer cells can be selectively captured.

BRIEF DESCRIPTION OF DRAWINGS

FIG. 1 shows an exemplary schematic view of a flow channel zone including a chamber zone.

DESCRIPTION OF EMBODIMENTS

The present invention relates to a medical analysis device including a flow channel zone that includes a chamber zone, and the inner surface of the flow channel zone is at least partially provided with a layer of a hydrophilic polymer having a thickness of 2 to 200 nm.

The medical analysis device of the present invention includes a flow channel zone that includes a chamber zone, and the inner surface of the flow channel zone is provided with a hydrophilic polymer layer having a specific thickness. In this device, the ability to capture specific cells such as cancer cells is greatly improved while the ability to capture platelets and others is reduced, as compared to cases where the inner surface of the flow channel zone is not provided with a hydrophilic polymer layer or is provided with a thicker hydrophilic polymer layer. Thus, the medical analysis device of the present invention has an effect of selectively capturing specific cells, which cannot be achieved at all in the above cases.

Exemplary preferred embodiments of the present invention will be described below referring to the FIGURE.

FIG. 1 shows an exemplary schematic view of a medical analysis device 1 of the present invention. The medical analysis device 1 includes a flow channel zone 11 in which a chamber zone 12 is provided. The inner surface of the flow channel zone 11 is entirely or partially provided (coated) with a hydrophilic polymer layer (not shown). It is suitable that the inner surface of the chamber zone 12 is entirely or partially, preferably entirely, provided with a hydrophilic polymer layer.

When blood or biological fluid is introduced into the flow channel zone 11, specific cells such as cancer cells present therein can be adsorbed to the hydrophilic polymer layer while adsorption of platelets, red blood cells, and others is reduced. Accordingly, specific cells such as cancer cells can be adsorbed to the hydrophilic polymer layer by introducing and retaining blood or biological fluid in the flow channel zone 11 for a predetermined time and then discharging it from the flow channel zone 11. Then, the number of specific cells such as cancer cells adsorbed can be counted to determine the number of specific cells in the blood or biological fluid, which is expected to be used, e.g., to confirm a cancer-treating effect.

Examples of the material of the flow channel zone 11 include acrylic resins (polyacrylic resins) such as polymethyl acrylate, polymethyl methacrylate, polyacrylic acid, and polymethacrylic acid, cycloolefin resin (polycycloolefin), carbonate resin (polycarbonate), styrene resin (polystyrene), polyester resins such as polyethylene terephthalate (PET), and polydimethylsiloxane.

The length L11 of the flow channel zone 11 (in the flow direction) and the (average) width R11 of the flow channel zone 11 except for the chamber zone 12 may be appropriately chosen according to the sample to be introduced. For example, when blood or biological fluid is introduced to selectively adsorb specific cells such as cancer cells, R11 is preferably 0.1 to 5 mm, more preferably 0.2 to 3 mm.

The shape (e.g. three-dimensional shape, substantially two-dimensional shape (bag-like shape)), size, and other conditions of the chamber zone 12 may be appropriately chosen according to the sample to be introduced.

The thickness of the hydrophilic polymer layer (layer formed of a hydrophilic polymer) is 2 to 200 nm, preferably 2 to 100 nm, more preferably 2 to 50 nm, still more preferably 2 to 30 nm. If the thickness is less than 2 nm, low adsorption of proteins and cells and selective adsorption or adhesion of cancer cells tend not to be well achieved. If the thickness is more than 200 nm, low adsorption of proteins and cells and selective adsorption or adhesion of cancer cells tend to deteriorate.

The hydrophilic polymer may be appropriately selected from polymers having hydrophilicity. In particular, it may suitably be a polymer that can form a polymer layer having a contact angle of 25° to 65° with water. For example, it may be a homopolymer or copolymer of one or two or more hydrophilic monomers, or a copolymer of one or two or more hydrophilic monomers with a second monomer. Specific examples include polyacrylic acid, polyacrylic acid esters, polymethacrylic acid, polymethacrylic acid esters, polyacryloylmorpholine, polymethacryloylmorpholine, polyacrylamide, and polymethacrylamide.

The hydrophilic monomer may be any monomer containing a hydrophilic group. Examples of the hydrophilic group include known hydrophilic groups such as an amide group, a sulfuric acid group, a sulfonic acid group, a carboxylic acid group, a hydroxy group, an amino group, and an oxyethylene group.

Specific examples of the hydrophilic monomer include (meth)acrylic acid, (meth)acrylic acid esters (e.g. alkoxyalkyl (meth)acrylates such as methoxyethyl (meth)acrylate, and hydroxyalkyl (meth)acrylates such as hydroxyethyl (meth)acrylate)), (meth)acrylamide, and (meth) acrylamide derivatives containing cyclic groups (e.g. (meth) acryloylmorpholine). Preferred among these are (meth)acrylic acid, (meth)acrylic acid esters, and (meth)acryloylmorpholine. Alkoxyalkyl (meth)acrylates are more preferred, with 2-methoxyethyl acrylate being particularly preferred.

The second monomer may be appropriately selected as long as it does not inhibit the effect of the hydrophilic polymer. Examples include aromatic monomers such as styrene, vinyl acetate, and N-isopropylacrylamide which can impart temperature responsiveness.

In the medical analysis device of the present invention, the inner surface of the flow channel zone is preferably provided with a layer of a superhydrophilic polymer in addition to or separately from the hydrophilic polymer layer. In this case, specific cells such as cancer cells can be adsorbed to the hydrophilic polymer layer while adsorption of platelets, red blood cells, and others is reduced by the superhydrophilic polymer layer. Thus, the medical analysis device has a superior effect in selectively capturing specific cells.

The superhydrophilic polymer layer may be formed of any polymer that can impart superhydrophilicity, such as a betaine polymer. Examples of the betaine polymer include polymers of betaine monomers and polymers of betaine monomers with monomers other than betaine monomers.

The betaine monomer may suitably be, for example, a carboxybetaine, sulphobetaine, or phosphobetaine. The monomer other than betaine monomers may be appropriately selected as long as it does not inhibit the effect of the superhydrophilic polymer layer. Examples include compounds listed for the hydrophilic monomer and the second monomer. Butyl methacrylate, among others, is preferred.

The medical analysis device of the present invention can be prepared, for example, by preparing a flow channel zone 11 illustrated in FIG. 1 in which the inner surface of the flow channel zone is entirely or partially provided with a hydrophilic polymer layer, optionally followed by addition of other members (parts).

Specifically, a polymer layer formed of a hydrophilic polymer may be provided by entirely or partially coating the inner surface of the flow channel zone 11 with a hydrophilic polymer solution or dispersion by a known method, such as (1) a method in which a hydrophilic polymer solution or dispersion prepared by dissolving or dispersing a hydrophilic polymer in any solvent, is injected into a flow channel zone 11 and retained for a predetermined time, or (2) a method in which the hydrophilic polymer solution or dispersion is applied (sprayed) to the inner surface of a flow channel zone 11. To the resulting flow channel zone are added other parts, if necessary. In this manner, a medical analysis device can be prepared.

The solvent, injection method, application (spraying) method, and other conditions may be conventionally known materials or methods.

The retention time in the method (1) or (2) may be appropriately chosen according to the size of the flow channel zone 11, the type of liquid introduced, or other factors, and is preferably five minutes to 10 hours, more preferably 10 minutes to five hours, still more preferably 15 minutes to two hours. After the retention, the excess hydrophilic polymer solution or dispersion may be discharged followed by drying, as required.

The chamber zone of the medical analysis device of the present invention may be a microchamber. When it is a microchamber, the width of the chamber zone is preferably 20 to 200 μm, and the number of chamber zones is preferably 100 to 500,000.

In the medical analysis device of the present invention, the inner surface of the flow channel zone preferably at least partially has a contact angle of 25° to 65°, more preferably 25° to 60° with water. With a predetermined contact angle with water, the effects of the present invention can be well achieved. Such a predetermined contact angle range with respect to water can be obtained, for example, by the use of the hydrophilic polymer layer described above.

As mentioned above, in the present invention, the inner surface of the flow channel zone is preferably provided with a layer of a superhydrophilic polymer in addition to or separately from the hydrophilic polymer layer. In this case, the superhydrophilic polymer layer preferably has a contact angle of 0° to 20° with water. This can improve selective capture of specific cells.

The medical analysis device of the present invention preferably further includes a filter structure, pillar structure, or dish structure (dish-like concave structure) for screening cells. Filters and pillars known in the art may be appropriately used.

The cell analysis method of the present invention includes examining cells such as cancer cells captured from blood or biological fluid using the above medical analysis device. For example, many cancer cells, including cancer cells not expressing EpCAM, can be captured by this method. Moreover, specific cells such as cancer cells can be sufficiently captured from blood or biological fluid, and adhesion or attachment of other proteins and cells can be reduced. Therefore, specific cells can be selectively captured.

In a suitable embodiment of the cell analysis method, blood from which platelets and red blood cells have previously been removed is introduced into the flow channel zone of the medical analysis device. This can further enhance the ability to selectively capture specific cells such as cancer cells. The removal of platelets and red blood cells may be carried out by known methods, such as centrifugation or membrane separation. Among these, centrifugation may suitably be used.

EXAMPLES

The present invention is specifically described with reference to examples below, but is not limited thereto.

Example 1

2-methoxyethyl acrylate was thermally polymerized at 80° C. for six hours using azobisisobutyronitrile (AIBN) to produce poly(2-methoxyethyl acrylate) (molecular weight Mn: about 15,000, Mw: about 50,000). Then, a 0.2% solution of the poly(2-methoxyethyl acrylate) in methanol was prepared.

The poly(2-methoxyethyl acrylate) solution (0.2% by mass) was injected into a flow channel made of polycycloolefin provided with a chamber zone as shown in FIG. 1, and allowed to stand for 30 minutes at room temperature. Thereafter, the solution was drawn using a pipette, followed by drying to prepare a medical analysis device (flow channel zone).

As to the polycycloolefin flow channel used, the length L11 of the flow channel zone, the width R11 of the flow channel zone except for the chamber zone, and the length L12 and width R12 of the chamber zone are as follows.
L11: 60 mm
R11: 1 mm
L12: 42 mm
R12: 9 mm

Example 2

A medical analysis device (flow channel zone) was prepared as in Example 1, except that the concentration of poly(2-methoxyethyl acrylate) was changed to 0.5% by mass.

Example 3

A medical analysis device (flow channel zone) was prepared as in Example 1, except that the concentration of poly(2-methoxyethyl acrylate) was changed to 1.0% by mass.

Example 4

A medical analysis device (flow channel zone) was prepared as in Example 1, except that the concentration of poly(2-methoxyethyl acrylate) was changed to 2.5% by mass.

Example 5

A medical analysis device (flow channel zone) was prepared as in Example 3, except that the polycycloolefin flow channel was replaced with a similar flow channel provided with a chamber zone, but made of polymethyl methacrylate.

Example 6

A medical analysis device (flow channel zone) was prepared as in Example 1, except that the concentration of poly(2-methoxyethyl acrylate) was changed to 5.0% by mass.

Comparative Example 1

A medical analysis device (flow channel zone) was prepared as in Example 1, except that no poly(2-methoxyethyl acrylate) solution (0.2% by mass) was injected so that no poly(2-methoxyethyl acrylate) layer was formed.

Comparative Example 2

A medical analysis device (flow channel zone) was prepared as in Example 1, except that the concentration of poly(2-methoxyethyl acrylate) was changed to 7.5% by mass.

Comparative Example 3

A medical analysis device (flow channel zone) was prepared as in Example 1, except that the concentration of poly(2-methoxyethyl acrylate) was changed to 10.0% by mass.

The medical analysis devices (flow channel zones) prepared in the examples and the comparative examples were evaluated in the following way.
(Thickness of Hydrophilic Polymer Layer (Coating Layer))

The thickness of the hydrophilic polymer layer on the inner surface of the flow channel zone was determined by measuring (photographing) the cross-section of the flow channel zone on which the hydrophilic polymer layer was formed using a TEM at an accelerating voltage of 15 kV and a magnification of ×1000.

(Amount of Platelets Adsorbed)

A liquid prepared by mixing plasma and platelets to adjust the concentration of platelets (plating density) to $4 \times 10^7$ cells/cm$^2$ was injected into the medical analysis device (flow channel zone), and allowed to stand at 37° C. for one hour. The inside of the device was washed with phosphate-buffered saline, followed by fixation using 1% glutaraldehyde (standing at 37° C. for two hours). Thereafter, the inside of the device was again washed with phosphate-buffered saline and distilled water.

This sample was observed by SEM, and the number of platelets adsorbed was counted. The number of platelets is expressed as a value relative to that of Comparative Example 1 which is taken as 1.

(Contact Angle with Water)

A volume of 2 µl of distilled water was dropped onto the inner surface of the flow channel zone. After 30 seconds from the dropping, the contact angle with water was measured by the θ/2 method at room temperature.

(Amount of Cancer Cells Adhered)

A suspension of human fibrosarcoma (HT1080: a type of cancer cell) (FBS, plating density: $1 \times 10^4$ cells/cm$^2$) was injected into the medical analysis device (flow channel zone), and allowed to stand at 37° C. for one hour. The inside of the device was washed with phosphate-buffered saline, followed by fixation using 1% glutaraldehyde (standing at 37° C. for two hours). Thereafter, the inside of the device was again washed with phosphate-buffered saline and distilled water.

This sample was observed by SEM, and the number of cancer cells adhered was counted. The number of cancer cells is expressed as a value relative to that of Comparative Example 1 which is taken as 1.

(Amount of White Blood Cells Adhered)

A suspension of white blood cells (FBS, plating density: $1 \times 10^4$ cells/cm$^2$) was injected into the medical analysis device (flow channel zone), and allowed to stand at 37° C. for one hour. The inside of the device was washed with phosphate-buffered saline, followed by fixation using 1% glutaraldehyde (standing at 37° C. for two hours). Thereafter, the inside of the device was again washed with phosphate-buffered saline and distilled water.

This sample was observed by SEM, and the number of white blood cells adhered was counted. The number of white blood cells is expressed as a value relative to that of Comparative Example 1 which is taken as 1.

TABLE 1

| | Example | | | | | |
|---|---|---|---|---|---|---|
| | 1 | 2 | 3 | 4 | 5 | 6 |
| Thickness of hydrophilic polymer layer (nm) | 2.5 | 7.5 | 32.5 | 85.9 | 48.5 | 180 |
| Amount of platelets adsorbed | 0.03 | 0.02 | 0.01 | 0.03 | 0.01 | 0.04 |
| Contact angle with water (°) | 56° | 50° | 43° | 41° | 38° | 62° |
| Amount of cancer cells adhered | 0.64 | 0.95 | 0.75 | 0.55 | 0.64 | 0.46 |
| Selectivity | 21.3 | 47.5 | 75.0 | 18.3 | 64.0 | 11.5 |
| Amount of white blood cells adhered | 0.05 | 0.06 | 0.02 | 0.01 | 0.06 | 0.01 |

TABLE 1-continued

| | Comparative Example | | |
|---|---|---|---|
| | 1 | 2 | 3 |
| Thickness of hydrophilic polymer layer (nm) | — | 280 | 450 |
| Amount of platelets adsorbed | 1 | 0.07 | 0.09 |
| Contact angle with water (°) | 89° | 67° | 70° |
| Amount of cancer cells adhered | 1 | 0.38 | 0.31 |
| Selectivity | 1.0 | 5.4 | 3.4 |
| Amount of white blood cells adhered | 1 | 0.11 | 0.14 |

Selectivity = Amount of cancer cells adhered/Amount of platelets adsorbed

With the medical analysis devices (flow channel zones) of the examples having a hydrophilic polymer layer (coating layer) with a specific thickness, the amount of platelets adsorbed was small while the amount of cancer cells adhered was large, and thus good selectivity (amount of cancer cells adhered/amount of platelets adsorbed) exceeding 10 was obtained. In contrast, the medical analysis device of Comparative Example 1 provided with no hydrophilic polymer layer exhibited low selectivity. The medical analysis devices of Comparative Examples 2 and 3 having a thicker layer were greatly inferior in selectivity to the examples because the amount of platelets adsorbed was slightly large and the amount of cancer cells adhered was slightly small. Also in the examples, the contact angle with water was 25° to 65°. These results demonstrated that the properties of low platelet adsorption and the properties of high cancer cell adhesion highly depend on the thickness of the hydrophilic polymer layer, and too large a thickness leads to greatly reduced selectivity. Furthermore, the amount of white blood cells adhered in the examples was also smaller than that in the comparative examples, and the selectivity was also good in this respect.

Accordingly, by adjusting the thickness of the hydrophilic polymer layer within the specific range of 2 to 200 nm, selectivity is improved so that the properties such as selectively capturing cancer cells from blood can be expected to be provided.

REFERENCE SIGNS LIST

1: Medical analysis device
11: Flow channel zone
12: Chamber zone
L11: Length of flow channel zone
L12: Length of chamber zone
R11: Width of flow channel zone 11 except for chamber zone
R12: Width of chamber zone

The invention claimed is:

1. A medical analysis device, comprising a flow channel zone that includes a chamber zone, wherein the whole or part of an inner surface of the flow channel zone is provided with a layer of a hydrophilic polymer which has a thickness of 2.5 to 180 nm and which has a water contact angle of 38° to 62°, and
    wherein the flow channel zone is formed from at least one material selected from the group consisting of acrylic resin and cycloolefin resin,
    wherein the medical analysis device selectively adheres cancer cells, and
    the hydrophilic polymer comprises alkoxyalkyl acrylates.

2. The medical analysis device according to claim 1, wherein the inner surface of the flow channel zone is provided with a layer of a superhydrophilic polymer having a water contact angle of 0° to 20° in addition to or separately from the hydrophilic polymer layer.

3. The medical analysis device according to claim 2, wherein the superhydrophilic polymer layer is formed of a betaine polymer.

4. The medical analysis device according to claim 1, further comprising a filter structure, pillar structure, or dish structure for screening cells.

5. A cell analysis method, comprising examining cells captured from blood or biological fluid using the medical analysis device according to claim 1.

6. The cell analysis method according to claim 5, wherein blood from which platelets and red blood cells have been removed is introduced into the flow channel zone of the medical analysis device.

7. The cell analysis method according to claim 6, wherein the removal of platelets and red blood cells is carried out by centrifugation.

* * * * *